(12) United States Patent
Chen et al.

(10) Patent No.: US 7,572,286 B1
(45) Date of Patent: Aug. 11, 2009

(54) STENT ASSEMBLY FOR THE TREATMENT OF VULNERABLE PLAQUE

(75) Inventors: Yung-Ming Chen, Cupertino, CA (US); Christopher Feezor, Mountain View, CA (US); Deborah Kilpatrick, Los Altos, CA (US); Santosh Prabhu, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1439 days.

(21) Appl. No.: 10/144,553

(22) Filed: May 13, 2002

(51) Int. Cl.
*A61F 2/06* (2006.01)

(52) U.S. Cl. .................. 623/1.13; 623/1.15; 623/1.42

(58) Field of Classification Search ............... 623/1.13, 623/1.16, 1.23, 1.35, 1.36, 1.11, 1.42; 606/194, 606/200
See application file for complete search history.

(56) References Cited

U.S. PATENT DOCUMENTS

| | | | | |
|---|---|---|---|---|
| 5,591,195 A | * | 1/1997 | Taheri et al. ............... | 623/1.11 |
| 5,653,747 A | * | 8/1997 | Dereume .................... | 623/1.54 |
| 5,824,046 A | | 10/1998 | Smith et al. | |
| 5,843,164 A | * | 12/1998 | Frantzen et al. ............ | 623/1.16 |
| 5,897,911 A | | 4/1999 | Loeffler | |
| 6,143,022 A | * | 11/2000 | Shull et al. ................. | 623/1.13 |
| 6,162,246 A | * | 12/2000 | Barone ....................... | 623/1.35 |
| 6,168,619 B1 | * | 1/2001 | Dinh et al. ................. | 623/1.13 |
| 6,319,278 B1 | * | 11/2001 | Quinn ........................ | 623/1.13 |
| 6,432,127 B1 | * | 8/2002 | Kim et al. .................. | 623/1.11 |
| 2002/0107561 A1 | | 8/2002 | Pinheiro | |

OTHER PUBLICATIONS

Beattie, D.K., Ph.D., *Mechanical Modeling: Assessing Atherosclerotic Plaque Behavior and Stability in Humans*, International Journal of Cardiovascular Medicine and Science, vol. 2, No. 2, pp. 69-81, 1999.

Cheng, George C., et al., *Distribution of Circumferential Stress in Ruptured and Stable Atherosclerotic Lesions: A Structural Analysis With Histopathological Correlation*, Circulation, vol. 87, No. 4, pp. 1179-1187, Apr. 1993.

Feezor, C., et al., *Integration of Animal and Human Coronary Tissue Testing With Finite Element Techniques for Assessing Differences in Arterial Behavior*, BED—Bioengineering Conference Amercian Society of Mechanical Engineers, vol. 50, pp. 135-136, Jun. 2001.

(Continued)

*Primary Examiner*—Anhtuan T Nguyen
*Assistant Examiner*—Kathleen Sonnett
(74) *Attorney, Agent, or Firm*—Fulwider Patton LLP

(57) ABSTRACT

An intravascular stent assembly for implantation in a body lumen, such as a coronary artery, is designed to treat a lesion with vulnerable plaque by reducing the fibrous cap stresses. A polymeric sleeve having first and second ends interconnects a first metallic stent and a second metallic stent. The first end is bonded to a distal end region of the first stent and the second end to a proximal end region of the second stent. The polymeric sleeve can be loaded with a therapeutic drug or agent to further control local thrombosis and/or induce healing if the plaque fibrous cap ruptures during or after implantation. Methods of making an intravascular stent assembly for the treatment of vulnerable plaque are also provided.

2 Claims, 4 Drawing Sheets

OTHER PUBLICATIONS

Lee, Richard T., et al., *Circumferential Stress and Matrix Metalloproteinase I in Human Coronary Atherosclerosis: Implications for Plaque Rupture, Arteriosclerosis, Thrombosis, and Vascular Biology*, vol. 16, No. 8, pp. 1070-1073, Aug. 1996.

Loree, Howard M., *Effects of Fibrous Cap Thickness on Peak Circumferential Stress in Model Atherosclerotic Vessels, Circulation Research*, vol. 71, No. 4, pp. 850-858, Oct. 1992.

Richardson, P.D., *Influence of Plaque Configuration and Stress Distribution on Fissuring of Coronary Atherosclerotic Plaques, The Lancet*, pp. 941-944, Oct. 21, 1989.

Veress, A.I., et al., *Finite Element Modeling of Atherosclerotic Plaque, IEEE*, The Cleveland Clinic Foundatino, The Ohio State University, Columbus, OH, pp. 701-794, 1993.

* cited by examiner

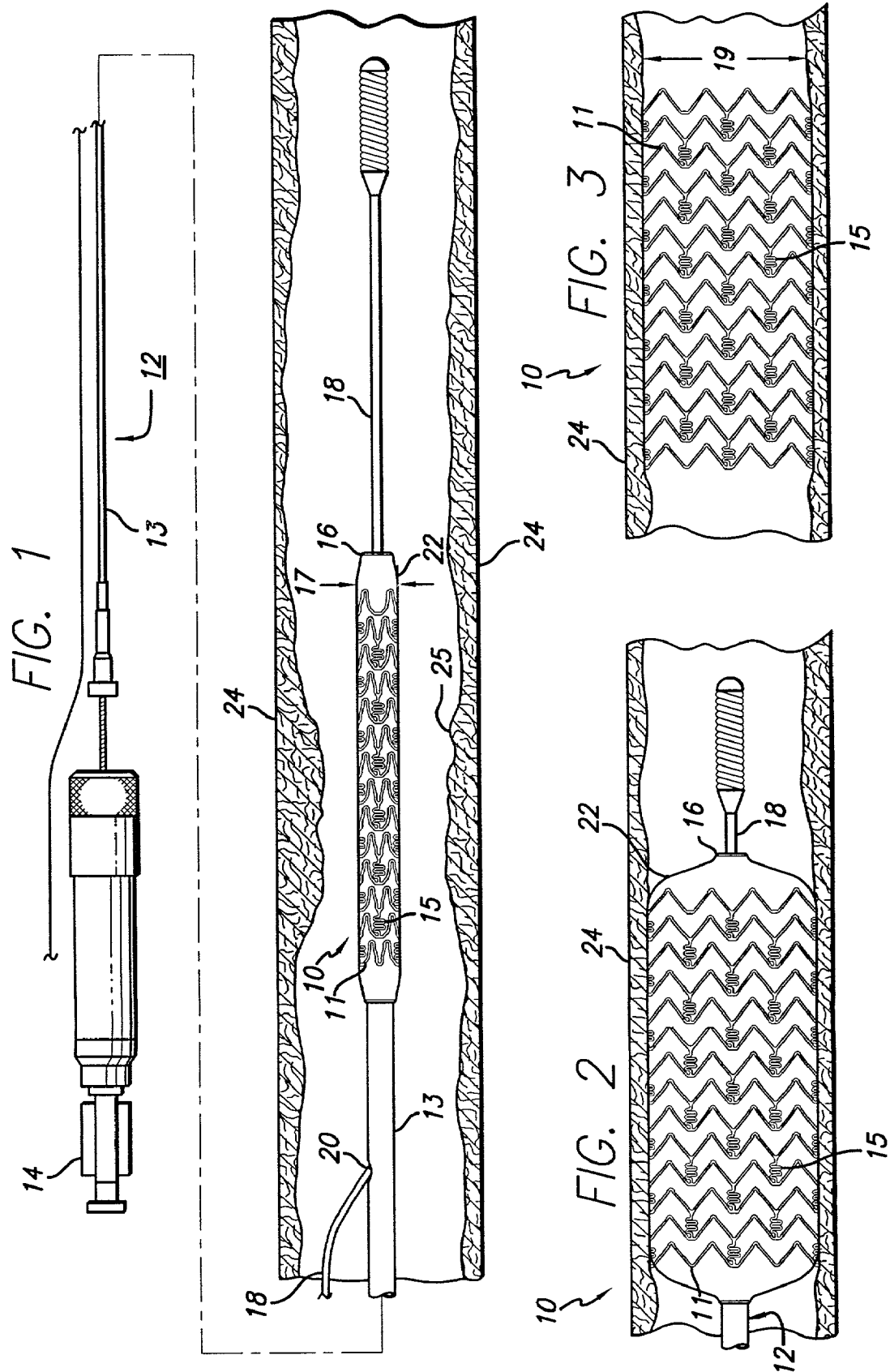

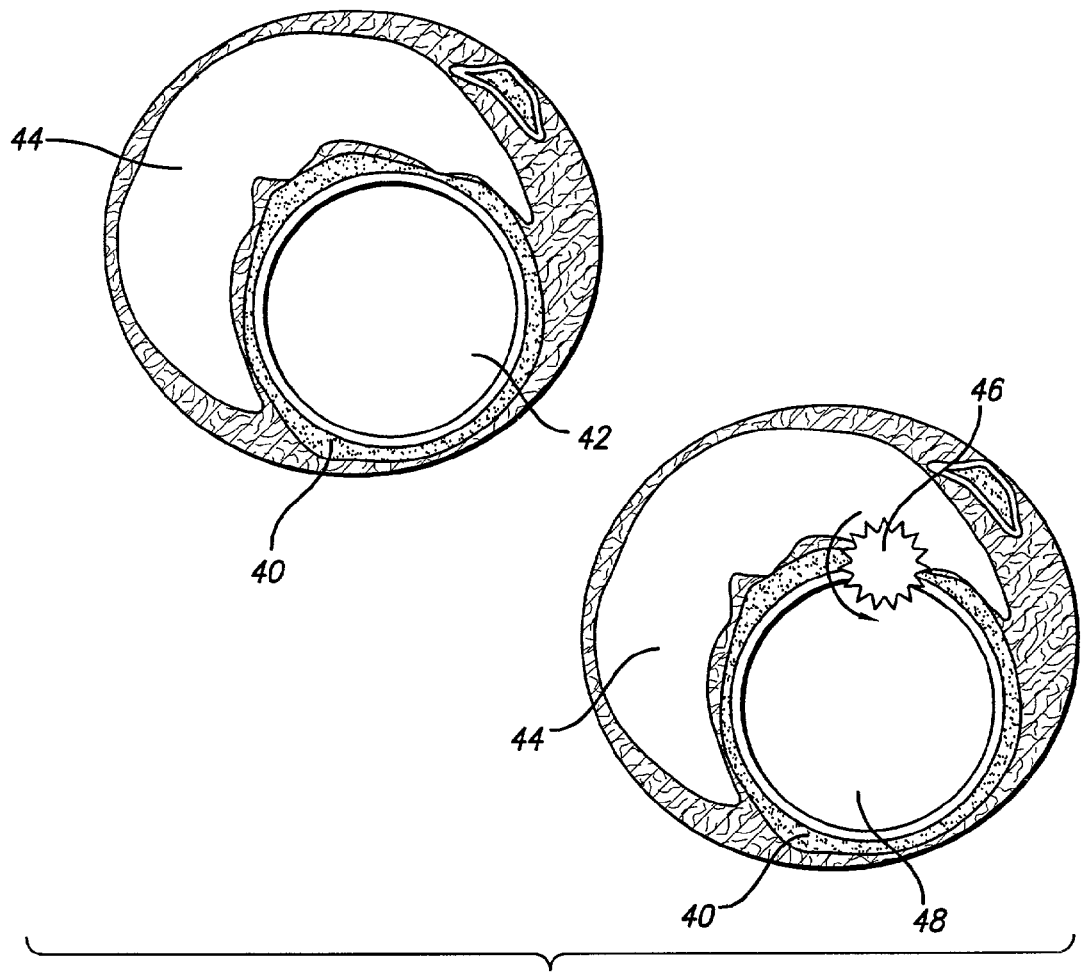
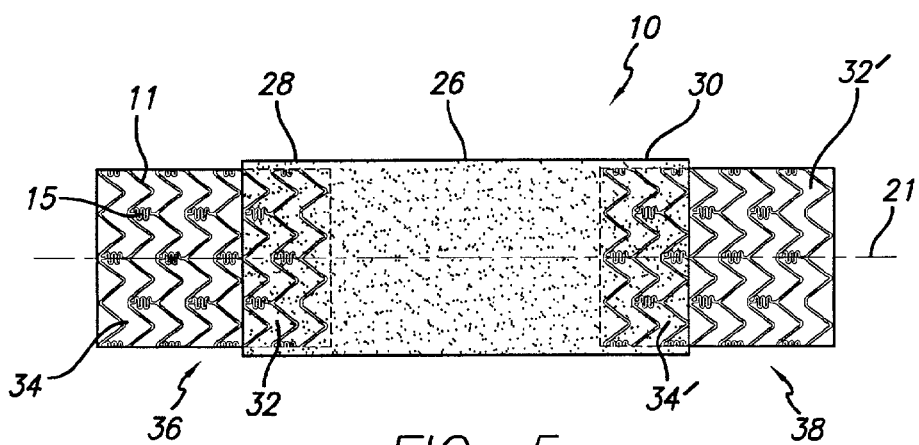

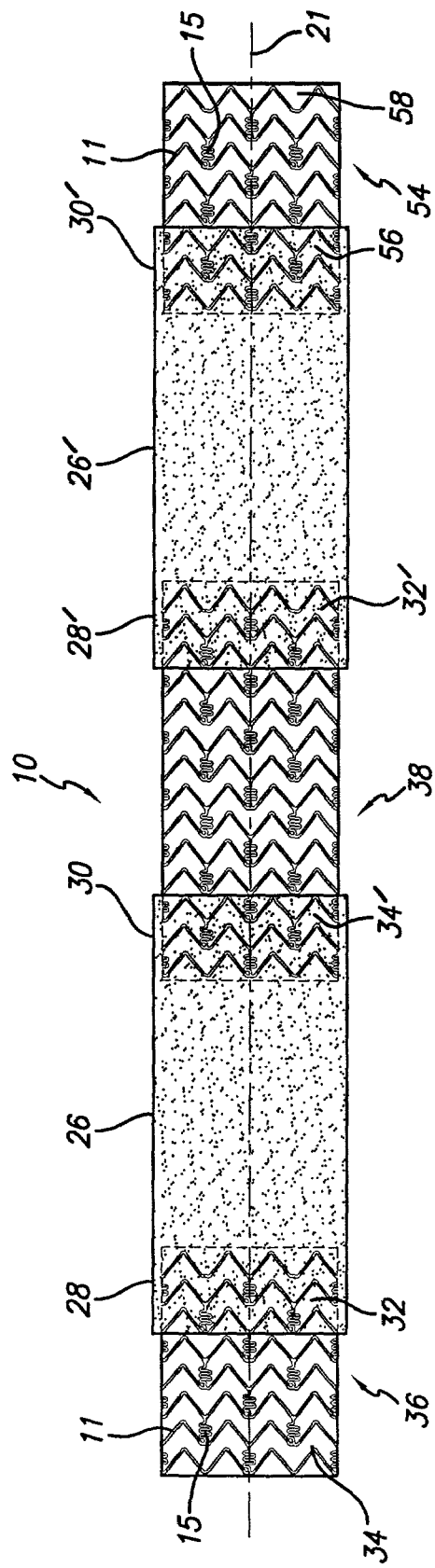
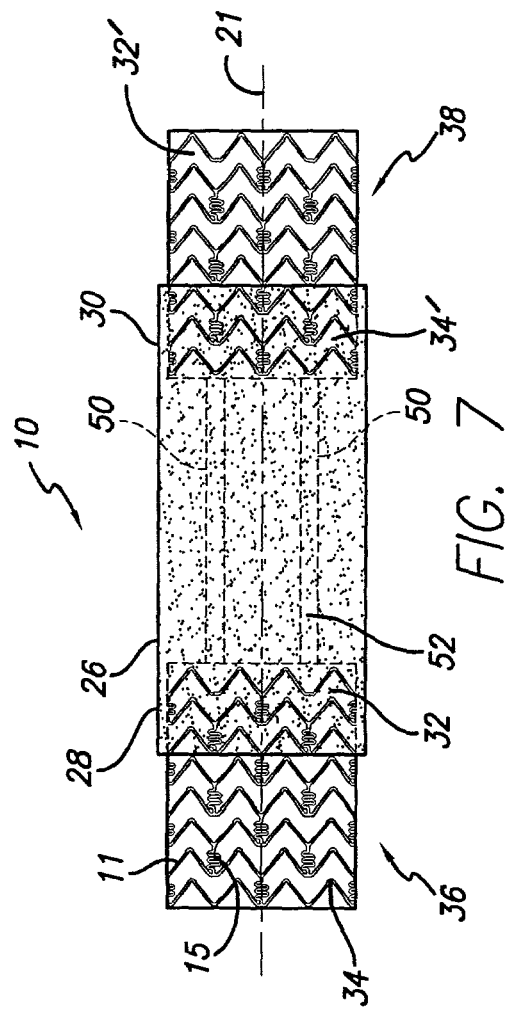
FIG. 6
FIG. 7

STENT ASSEMBLY FOR THE TREATMENT OF VULNERABLE PLAQUE

BACKGROUND OF THE INVENTION

The present invention relates to vascular repair devices, and in particular to intravascular stents, which are adapted to be implanted into a patient's body lumen, such as a blood vessel or coronary artery, for the treatment of unstable or vulnerable, human atherosclerotic plaque.

Currently, the treatment of unstable or vulnerable plaque presents a significant therapeutic challenge to medical investigators. Vulnerable plaque is characterized by a basic lesion which is a raised plaque beneath the innermost arterial layer, the intima. Atherosclerotic plaques are primarily composed of varying amounts of long chain extracellular matrix (ECM) proteins that are synthesized by smooth muscle cells. The other primary lesion component of atherosclerotic plaque includes lipoproteins, existing both extracellularly and within foam cells derived primarily from lipid-laden macrophages. In a more advanced lesion, a necrotic core may develop, consisting of lipids, foam cells, cell debris, and cholesterol crystals, and myxomatous configurations with crystalline lipid forms. The necrotic core is rich in tissue factor and quite thrombogenic, but in the stable plaque it is protected from the luminal blood flow by a robust fibrous cap composed primarily of long chain ECM proteins, such as elastin and collagen, which maintain the strength of the fibrous cap. The aforementioned plaque represents the most common form of vulnerable plaque, known as a fibroatheroma. Histology studies from autopsy suggest this form constitutes the majority of vulnerable plaques in humans. A second form of vulnerable plaque represents a smaller fraction of the total, and these are known as erosive plaques. Erosive plaques generally have a smaller content of lipid, a larger fibrous tissue content, and varying concentrations of proteoglycans. Various morphologic features that have been associated with vulnerable plaque, include thinned or eroded fibrous caps or luminal surfaces, lesion eccentricity, proximity of constituents having very different structural moduli, and the consistency and distribution of lipid accumulations. With the rupture of fibroatheroma forms of vulnerable plaque, the luminal blood becomes exposed to tissue factor, a highly thrombogenic core material, which can result in total thrombotic occlusion of the artery. In the erosive form of vulnerable plaque, mechanisms of thrombosis are less understood but may still yield total thrombotic occlusion.

Although rupture of the fibrous cap in a fibroatheroma is a major cause of myocardial infarction (MI) related deaths, there are currently no therapeutic strategies in place to treat lesions that could lead to acute MI. The ability to detect vulnerable plaques and to treat them successfully with interventional techniques before acute MI occurs has long been an elusive goal. Numerous finite element analysis (FEA) studies have proved that, in the presence of a soft lipid core, the fibrous cap shows regions of high stresses. Representative of these studies include the following research articles, each of which are incorporated in their entirety by reference herein: Richardson et al. (1989), Influence of Plaque Configuration and Stress Distribution on Fissuring of Coronary Atherosclerotic Plaques, Lancet, 2(8669), 941-944; Loree et al. (1992), Effects of Fibrous Cap Thickness on Circumferential Stress in Model Atherosclerotic Vessels, Circulation Research, 71, 850-858; Cheng et al. (1992), Distribution of Circumferential Stress in Ruptured and Stable Atherosclerotic Lesions: A Structural Analysis With Histopathological Correlation, Circulation, 87, 1179-1187; Veress et al. (1993), Finite Element Modeling of Atherosclerotic Plaque, Proceedings of IEEE Computers in Cardiology, 791-794; Lee et al. (1996), Circumferential Stress and Matrix Metalloproteinase 1 in Human Coronary Atherosclerosis: Implications for Plaque Rupture, Atherosclerosis Thrombosis Vascular Biology, 16, 1070-1073; Vonesh et al. (1997), Regional Vascular Mechanical Properties by 3-D Intravascular Ultrasound Finite-Element Analysis, American Journal of Physiology, 272, 425-437; Beattie et al. (1999), Mechanical Modeling: Assessing Atherosclerotic Plaque Behavior and Stability in Humans, International Journal of Cardiovascular Medical Science, 2(2), 69-81; and Feezor et al. (2001), Integration of Animal and Human Coronary Tissue Testing with Finite Element Techniques for Assessing Differences in Arterial Behavior, BED-Vol. 50, 2001 Bioengineering Conference, ASME 2001. Further, these studies have indicated that such high stress regions correlate with the observed prevalence of locations of cap fracture. Moreover, it has been shown that subintimal structural features such as the thickness of the fibrous cap and the extent of the lipid core, rather than stenosis severity are critical in determining the vulnerability of the plaque. The rupture of a highly stressed fibrous cap can be prevented by using novel, interventional, therapeutic techniques such as specially designed stents that redistribute and lower the stresses in the fibrous cap.

Stents are generally tubular-shaped devices which function to hold open a segment of a blood vessel, coronary artery, or other body lumen. They are particularly suitable for use to support and hold back a dissected arterial lining which can occlude the fluid passageway therethrough.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter. One of the difficulties encountered using prior art stents involved maintaining the radial rigidity needed to hold open a body lumen while at the same time maintaining the longitudinal flexibility of the stent to facilitate its delivery. Once the stent is mounted on the balloon portion of the catheter, it is often delivered through tortuous vessels, including tortuous coronary arteries. The stent must have numerous properties and characteristics, including a high degree of flexibility, in order to appropriately navigate the tortuous coronary arteries. This flexibility must be balanced against other features including radial strength once the stent has been expanded and implanted in the artery. While other numerous prior art stents have had sufficient radial strength to hold open and maintain the patency of a coronary artery, they have lacked the flexibility required to easily navigate tortuous vessels without damaging the vessels during delivery.

Generally speaking, most prior art intravascular stents are formed from a metal such as stainless steel, which is balloon expandable and plastically deforms upon expansion to hold open a vessel. The component parts of these types of stents typically are all formed of the same type of metal, i.e., stainless steel. Other types of prior art stents may be formed from a polymer, again all of the component parts being formed from the same polymer material. These types of stents, the ones formed from a metal and the ones formed from a polymer, each have advantages and disadvantages. One of the advantages of the metallic stents is their high radial strength once expanded and implanted in the vessel. A disadvantage may be that the metallic stent lacks flexibility which is important during the delivery of the stent to the target site. With respect to polymer stents, they may have a tendency to be quite flexible and are advantageous for use during delivery through tortuous vessels, however, such polymer stents may lack the radial strength necessary to adequately support the lumen once implanted into an occlusive fibromuscular lesion of 70% stenosis or greater.

What has been needed and heretofore unavailable is a stent that can be used to treat a vulnerable plaque by reducing the cap stresses. The present invention satisfies this need and others.

SUMMARY OF THE INVENTION

The present invention is directed to an intravascular stent assembly that can be used to treat a lesion with vulnerable plaque by reducing the cap stresses. The invention also includes methods of making an intravascular stent assembly for the treatment of vulnerable plaque within an artherosclerotic artery and methods of using the stent assembly for the treatment of the same.

The stent assembly embodying features of the invention can be readily delivered to the desired body lumen, such as a coronary artery (peripheral vessels, bile ducts, etc.), by mounting the stent assembly on an expandable member of a delivery catheter, for example a balloon, and advancing the catheter and stent assembly through the body lumen to the target site. Generally, the stent is compressed or crimped onto the balloon portion of the catheter so that the stent assembly does not move longitudinally relative to the balloon portion of the catheter during delivery through the arteries, and during expansion of the stent at the target site. The stent is relatively flexible along its longitudinal axis to facilitate delivery through tortuous body lumens yet is stiff and stable enough radially in an expanded condition to maintain the patency of a body lumen such as an artery when implanted therein.

In one embodiment, the stent assembly of the invention generally includes a polymeric sleeve portion in a tubular configuration having first and second ends, wherein the first end is attached to a distal end region of a first stent and the second end is attached to a proximal end region of a second stent. The first and second stents of the stent assembly include a plurality of radially expandable cylindrical rings which are relatively independent in their ability to expand and to flex relative to one another. The individual radially expandable cylindrical rings of the stent are formed from a metallic material and are aligned on a common longitudinal axis. The resulting stent assembly structure is a series of radially expandable cylindrical rings, which are spaced longitudinally close enough so that small dissections in the wall of a body lumen may be pressed back into position against the luminal wall, but not so close as to compromise the longitudinal flexibility of the stent assembly. The cylindrical rings are attached to each other by flexible links such that at least one flexible link attaches adjacent cylindrical rings. If desired, more than one link can be used to attach adjacent cylindrical rings.

In an alternative embodiment, the stent assembly of the present invention includes at least two polymeric sleeve portions that are interconnected by at least three separate stents to form the stent assembly.

In another embodiment, the metallic material forming the stent includes stainless steel, titanium, tantalum, nickel titanium, and cobalt-chromium. The polymer material forming the polymeric sleeve portion is taken from a select group of biodegradable, bioabsorbable polymers or those with drug eluting capability for appropriate therapeutic drugs. Examples of preferable therapeutic drugs include antiplatelets, anticoagulants, antifibrins, antithrombins, and antiproliferatives.

The polymeric sleeve portion of the stent assembly has a length in a range of about 1 to 20 mm, and a thickness in the range of about 0.001 to 0.010 inches. The thickness of the polymeric sleeve portion is preferably in the range of about 0.001 to 0.005 inch.

In another embodiment, the polymeric sleeve portion is in communication with each of the metallic portions of the first and second stents by being mechanically fastened thereto. A primer is disposed about the metallic portion of the first and second stents that contacts the polymeric sleeve portion. The medium by which the polymeric sleeve portion is attached to the metallic portion of the stent assembly involves the application of a silicone adhesive on the metallic portion that contacts the polymeric sleeve which is cured thereon. Further, the polymeric sleeve portion of the stent assembly can be optionally loaded with at least one therapeutic drug or agent. Alternatively, if at least three stents are used, then at least two polymer sleeve portions are mechanically fastened to each of the metallic portions of the first, second and third stents as described above.

In still another embodiment, at least two links, but preferably no more than three links, interconnect the separate stent sections, while being in direct communication with the polymer sleeve portion in order to provide additional support to the sleeve portion.

One method for making the stent assembly of the present invention for use in the treatment of vulnerable plaque includes providing a first metallic stent and a second metallic stent having a generally cylindrical shape, wherein both the first metallic stent and the second metallic stent have distal and proximal end regions. A primer is applied to the distal end region of the first metallic stent and to the proximal end region of the second metallic stent. A first end of a tubular sleeve preformed of a polymer material is fitted onto the distal end region of the first metallic stent and a second end of the sleeve onto the proximal end region of the second metallic stent. An adhesive (e.g., silicone) is then applied over the portion of the polymeric sleeve that contacts the metallic portion of the stent assembly. The polymeric sleeve is bonded to the metallic portions of both the first and second stents.

Preferably, the metallic materials forming the stent assembly consist of stainless steel, titanium, tantalum, nickel titanium, and cobalt-chromium. The polymer material forming the sleeve is preferably taken from a select group of biodegradable bioabsorbable polymers or those with drug eluting capability for appropriate therapeutic drugs. Examples of preferable therapeutic drugs include antiplatelets, anticoagulants, antifibrins, antithrombins, and antiproliferatives.

The process by which the polymer sleeve is preferably bonded to the metallic portions of the stent assembly involves curing with heat. The stent assembly is cured in an oven at about 150° C. for about 15 minutes and then cooled down for about 5 to 20 minutes. The polymer sleeve can be optionally loaded with at least one therapeutic drug or agent.

Methods of using an intravascular stent assembly for treatment of a vulnerable plaque region within a body lumen are also provided herein.

Other features and advantages of the present invention will become more apparent from the following detailed description of the invention when taken in conjunction with the accoMPanying exemplary drawings.

BRIEF DESCRIPTION OF THE DRAWINGS

FIG. 1 is an elevational view, partially in section, of a stent embodying features of the invention which is mounted on a delivery catheter and disposed within a damaged artery.

FIG. 2 is an elevational view, partially in section, similar to that shown in FIG. 1 wherein the stent is expanded within a damaged or diseased artery.

FIG. 3 is an elevational view, partially in section, depicting the expanded stent within the artery after withdrawal of the delivery catheter.

FIG. 4 is a schematic of a process of fibrous cap rupture in a fibroatheroma form of vulnerable plaque leading to a thrombotic occlusion of an artery.

FIG. 5 is a schematic view of one embodiment of a stent assembly with a polymer sleeve portion in accordance with the present invention.

FIG. 6 is a schematic view of an alternative embodiment of a stent assembly having at least two polymeric sleeve portions interconnected by three stents.

FIG. 7 is a schematic view of another alternative embodiment of a stent assembly having at least two links interconnecting the first and second stents.

DETAILED DESCRIPTION OF THE PREFERRED EMBODIMENTS

Figure 8:
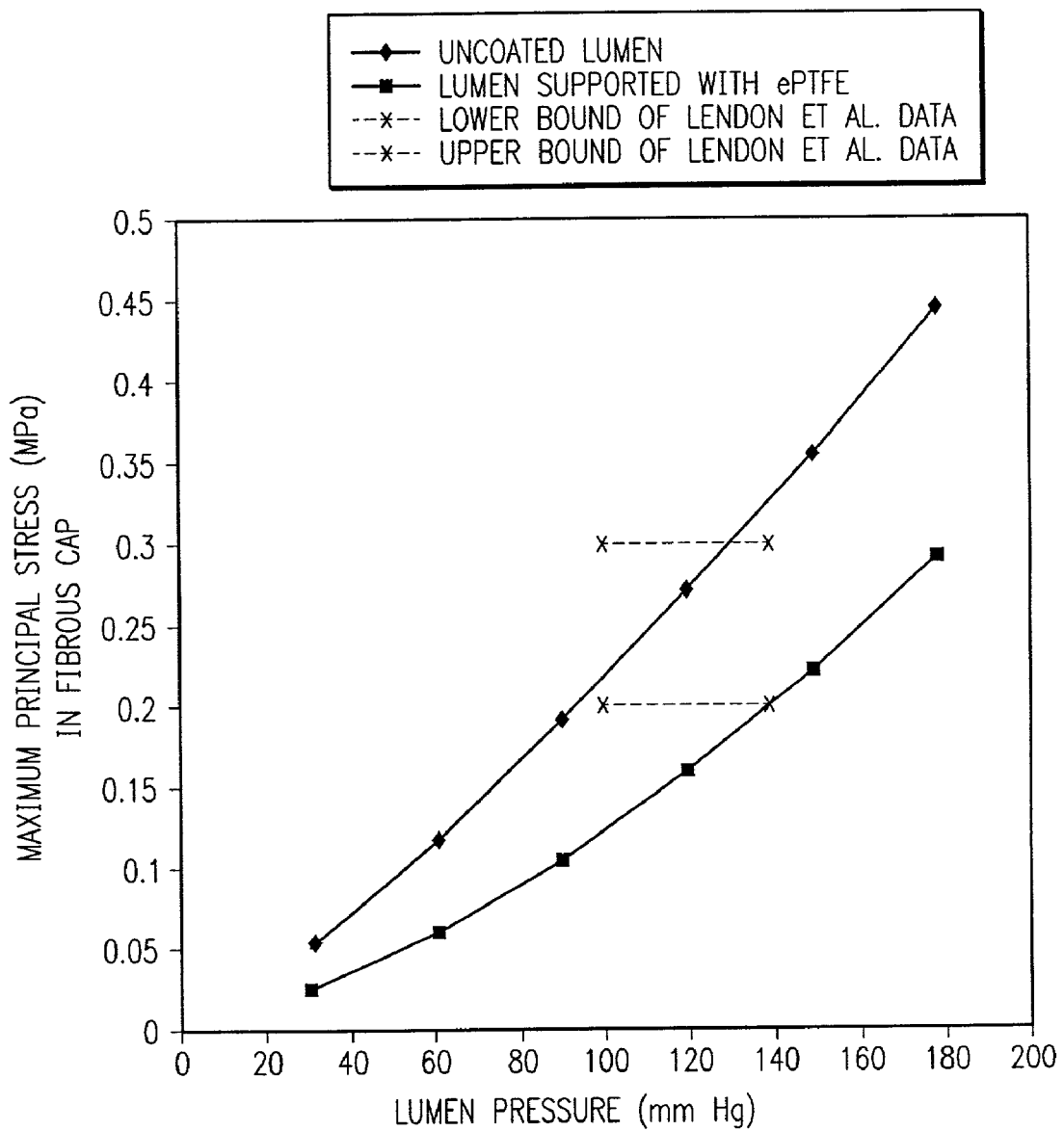
FIG. 8 is a graph depicting the stress-lowering effect of the addition of polymer scaffolding on the maximum principal stress in the fibrous cap of a fibroatheroma form of vulnerable plaque.

The stent assembly of the present invention serves to treat a lesion with vulnerable plaque by reducing the cap stresses. The embodiments set forth herein describe a first metallic stent 36 interconnected to a second metallic stent 38 by a polymeric sleeve portion 26 (FIG. 5) to thereby form the stent assembly of the present invention. Further, methods of fabricating a stent assembly for the treatment of vulnerable plaque and methods of using the stent assembly for the treatment of the same are also disclosed herein.

Turning to the drawings, FIG. 1 depicts a metallic stent 10 incorporating features of the invention (shown without a polymer sleeve portion 26 (FIG. 5)) mounted on a catheter assembly 12 which is used to deliver the stent and implant it in a body lumen, such as a coronary artery, peripheral artery, or other vessel or lumen within the body. The stent generally includes a plurality of radially expandable cylindrical rings 11 disposed generally coaxially and interconnected by undulating links 15 disposed between adjacent cylindrical elements. The catheter assembly includes a catheter shaft 13 which has a proximal end 14 and a distal end 16. The catheter assembly is configured to advance through the patient's vascular system by advancing over a guide wire by any of the well known methods of an over the wire (OTW) system (not shown) or a well known rapid exchange (RX) catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent assembly 10 of the present invention is used to repair a diseased or damaged arterial wall which may include the plaque 25 as shown in FIG. 1, or a dissection, or a flap which are commonly found in the coronary arteries, peripheral arteries and other vessels.

In a typical procedure to implant stent assembly 10, the guide wire 18 is advanced through the patient's vascular system by well known methods so that the distal end of the guide wire is advanced past the plaque or diseased area 25. Prior to implanting the stent assembly, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent assembly is positioned in the target area. The expandable member or balloon 22 is inflated by well known means so that it expands radially outwardly and in turn expands the stent assembly radially outwardly until the stent assembly is apposed to the vessel wall. The expandable member is then deflated and the catheter withdrawn from the patient's vascular system. The guide wire typically is left in the lumen for post-dilatation procedures, if any, and subsequently withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 serves to hold open the artery 24 after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. Both the metallic and polymeric sleeve portions of the stent will eventually become endothelialized. It is this endothelialization and subsequent neointimal growth that will integrate the device into the fibrous cap portion of the vulnerable plaque. This integration will yield lower fibrous cap stresses overall, as predicted by simulations shown in FIG. 6. The undulating portion of the stent provides good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery, as illustrated in FIGS. 2 and 3.

The stent patterns shown in FIGS. 1-3 are for illustration purposes only and can vary in size and shape to accommodate different vessels or body lumens. Further, the metallic stent 10 is of a type that can be used in accordance with the present invention. As described in further detail below, a first stent 36 is interconnected to a second stent 38 by a polymeric sleeve portion 26 (FIG. 5) to thereby form the stent assembly of the present invention.

The links 15 which interconnect adjacent cylindrical rings 11 may have a transverse cross-section similar to the transverse dimensions of the undulating components of the expandable cylindrical rings. In one embodiment, all of the links are joined at either the peaks or the valleys of the undulating structure of the cylindrical rings. In this manner there is little or no shortening of the stent assembly upon expansion.

The number and location of links 15 connecting the rings 11 can be varied in order to vary the desired longitudinal and flexural flexibility in the stent assembly structure both in the unexpanded as well as the expanded condition. These properties are important to minimize alteration of the natural physiology of the body lumen into which the stent assembly is implanted and to maintain the compliance of the body lumen which is internally supported by the stent assembly. Generally, the greater the longitudinal and flexural flexibility of the stent assembly, the easier and the more safely it can be delivered to the target site.

FIG. 4 illustrates a schematic of a process of fibrous cap rupture in a fibroatheroma form of vulnerable plaque leading to a thrombotic occlusion of an artery 24 (FIG. 1). A patent lumen 42 at the lesion site is separated from a lipid core 44 of the lesion by the fibrous cap 40. As discussed earlier, when the fibrous cap is ruptured 46, the lumenal blood becomes exposed to tissue factor, a highly thrombogenic core material, which can result in total thrombotic occlusion 48 of the artery. The intravascular stent assembly of the present invention is a novel, interventional, therapeutic technique that redistributes and lowers the stresses in the fibrous cap.

In one embodiment shown in FIG. 5, the stent assembly 10 of the present invention has a plurality of flexible cylindrical rings 11 being expandable in a radial direction, with each of the rings having a first delivery diameter 17 (FIG. 1) and a second implanted diameter 19 (FIG. 3) and being aligned on a common longitudinal axis 21. At least one link 15 is attached between adjacent rings to form the metallic portion of the stent. Preferably, each of the rings is formed of a metallic material. However, the stent assembly of the present invention is not limited to the use of such metallic materials as non-metallic materials are also contemplated for use with the invention. As shown in FIG. 5, the polymeric sleeve portion 26 is tubular in configuration having a first end 28 and a second end 30, wherein the first end is attached to a distal end region 32 of a first metallic stent 36 and the second end is attached to a proximal end region 34' of a second metallic stent 38. Because the length of a characteristic vulnerable plaque region 25 is generally in the range of about 3 to 30 mm, it is preferable that the length of the polymeric sleeve portion is slightly longer than the vulnerable plaque region. Preferably, the length of the polymeric sleeve portion is in the range of about 3 to 15 mm and in any event should be long enough to cover the vulnerable plaque region. Thus, for some applications, sleeve 26 may be longer or shorter than the disclosed range. The polymeric sleeve portion can be fabricated in a multiplicity of sizes in order to accommodate multiple lengths of lesions containing vulnerable plaque that require treatment. The polymeric sleeve portion can have a thickness in the range of about 0.001 to 0.010 inch. The thickness of the polymer sleeve portion is preferably in the range of about 0.001 to 0.005 inch. The thickness of the polymeric sleeve portion can vary depending on whether the polymeric sleeve is loaded with a therapeutic drug or agent. The sleeve can be loaded asymmetrically with drug or agent according to plaque geometry. Accordingly, the polymeric sleeve portion generally has a greater thickness with the incorporation of therapeutic drugs or agents therein.

The stent assembly of the present invention is placed in an artherosclerotic artery such that upon deployment the polymeric sleeve apposes the region containing the vulnerable plaque. With further reference to FIG. 5, the polymeric sleeve portion 26 of the stent assembly apposes the treatment site (not shown) within the body lumen while the rings are in the implanted diameter (FIG. 3). This configuration could be applicable for at least two reasons. First, given that previous studies have suggested that many vulnerable plaques are not occlusive prior to the thrombotic event, these plaques could require less scaffolding strength than typical metallic stents are designed to provide. Second, in the event of cap rupture within the plaque, the polymeric sleeve would provide high coverage and focal drug delivery to the rupture region. For purposes of this invention, the treatment site is preferably an artery 24 having at least one lesion containing vulnerable plaque 25 (FIG. 1).

In keeping with the invention, the polymeric sleeve portion 26 (FIG. 5) is formed from a flexible polymer material, preferably expanded polytetrafluoro-ethylene (ePTFE) or certain microporous forms of ultra high molecular weight polyethylene (UHMWPE) or polypropylene, or PVDF, that is bendable and flexible to enhance longitudinal and flexural flexibility of the stent assembly 10. The polymer materials, ePTFE, PVDF, UHMWPE and polypropylene, are characterized by a node and fibril microstructure. The porous node and microfibril microstructure can be produced in these polymer materials by using conventional methods that heat, coMPact and stretch the materials. The polymeric sleeve portion serves as scaffolding in keeping the artery 24 (FIG. 1) open like a conventional metallic stent. In addition, the polymeric sleeve also provides reinforcement to the thin fibrous cap and reduces the stresses therein once endothelialization has integrated the sleeve with tissue. One study in particular, by Lendon et al. (1993) Testing of Small Connective Tissue Specimens for the Determination of the Mechanical Behavior of Artherosclerotic Plaques, Journal of Biomedical Engineering, 15(1), 27-33, showed that the ultimate strength of human plaque fibrous cap material was in the range of 0.2-0.3 MPa. Standard finite element methods can be used to predict peak stresses in a fibrous cap using plaque component material property data from Beattie et al. (1998), Mechanical Analysis of Heterogeneous, Atherosclerotic Human Aorta, Journal of Biomechanical Engineering, in a two dimensional plaque model. It can be shown that the presence of an ePTFE polymer sleeve will reduce maximum principal stress at systole in the fibrous cap to a level well below the ultimate strength measured by Lendon et al. This is in contrast to scaffolding devices with open cells which could yield localized stress concentrations in the regions where the device edges contact the arterial walls. In the event of a cap rupture, the use of the polymeric sleeve portion 26 in accordance with the present invention is particularly advantageous. Accordingly, although the polymeric sleeve portion 26 can be microporous (depending on the physical property of the polymeric material selected), the polymeric sleeve portion prevents the lipid contents of vulnerable plaque from embolizing in the artery 24 lumen. Any drug or agent eluting from the sleeve would also act to initiate stabilizing responses and healing at the rupture site.

In an alternative embodiment as shown in FIG. 6, the stent assembly 10 of the present invention is formed from first and a second polymeric sleeve portions 26 and 26' interconnected by at least three separate stent portions 36, 38 and 54. This particular arrangement is advantageous for treating adjacent vulnerable plaque regions within the body lumen. The first and second polymeric sleeve portions are tubular in configuration, the first polymeric sleeve portion having a first end 28 and a second end 30, wherein the first end is attached to a distal end region 32 of a first metallic stent 36 and the second end is attached to a proximal end region 34' of a second metallic stent 38. A second polymeric sleeve portion has a first end 28' and a second end 30', wherein the first end 28' is attached to a distal end region 32' of the second metallic stent and the second end 30' is attached to a proximal end region 56 of a third metallic stent 54.

In another alternative embodiment as shown in FIG. 7, the stent assembly includes at least two metallic links 50, but preferably no more than three metallic links, that interconnect the first and second stents 36, 38 and are in direct communication with the polymer sleeve portion 26 to provide additional support to the polymer sleeve portion while positioned within the body lumen to repair a diseased or damaged arterial wall (not shown). Because the at least two metallic links 50 are formed from a metal material, the polymeric sleeve portion must be mechanically fastened to an outside surface area 52 of the at least two links. The process for mechanically fastening the polymeric sleeve portion to the metallic stent sections set forth above is also applicable to this embodiment.

For each of the embodiments set forth above, because the cylindrical rings 11 and links 15 can be formed out of a metal, such as stainless steel or the like, the polymeric sleeve portion 26 must be attached to each of the respective first and second metallic stent portions 36, 38. The polymeric sleeve portion of the stent assembly 10 is in direct communication with the metallic portions of the stent assembly by being mechanically fastened thereto. A primer is disposed about the metallic portions of both the first and second stents that contacts the polymeric sleeve portion. A silicone adhesive, disposed about the metallic portions that contact the polymeric sleeve and cured thereon, is the medium by which the polymeric sleeve portion is mechanically attached to the metallic portions of the stent assembly.

One other aspect of the invention provides for a method of fabricating an intravascular stent assembly 10 for use within a body lumen for the treatment of vulnerable plaque 25 (FIG. 1). In a preferred embodiment, a first metallic stent 36 and a second metallic stent 38 having a generally cylindrical shape, is provided, wherein both the first metallic stent and the second metallic stent have respective distal and proximal end regions 32, 34 and 32', 34'. A primer is preferably applied to the distal end region 32 of the first metallic stent 36 and to the proximal end region 34' of the second metallic stent 38. Examples of preferred primers that can be used include parylene, primacor (a copolymer of ethylene and acrylic acid), and EVAL (a copolymer of ethylene and vinyl alcohol).

A first end 28 of a sleeve 26, tubular in configuration and preformed of a polymer material, is fitted onto the distal end region 32 of the first metallic stent 36 and a second end 30 of the sleeve onto the proximal end region 34' of the second metallic stent 38. An adhesive is then applied over the portion of the polymeric sleeve 26 that contacts the metallic portions 36, 38 of the stent assembly 10. One example of a preferable adhesive is silicone. Thereafter, the polymeric sleeve is bonded to the metallic portions of the stent assembly through curing.

Following the application of the silicone adhesive to select areas of the stent assembly 10, the polymeric sleeve 26 is bonded to the metallic portions 36, 38 of the stent assembly through a process referred to as curing. Preferably, the stent assembly of the present invention is oven cured at a temperature of about 150° C. for a duration of about 15 minutes. As a result of the stent assembly being subjected to such high temperatures during the curing process, the silicone adhesive seeps through the ePTFE or UHMWPE matrix and over the edges of the polymeric sleeve to thereby attach to the metallic portions of the stent assembly. The stent assembly is thereafter cooled down for approximately 5 to 20 minutes. Accordingly, the curing process is the medium by which the polymeric sleeve portion is mechanically fastened to the metallic portions of the stent.

Any variety of stent configurations may be subjected to the bonding process described herein, including, but not limited to, the Multi-Link® generation stents manufactured and sold by Advanced Cardiovascular Systems, Inc. of Santa Clara, Calif. The metals from which such stents are formed may include stainless steels, titanium, tantalum, nickel titanium, and cobalt-chromium, among others.

The polymeric material of the invention preferably comprises a biodegradable, bioabsorbable polymeric material or one with drug eluting capability for appropriate therapeutic drugs. The polymeric materials preferably include, but are not limited to, polycaprolactone (PCL), poly-DL-lactic acid (DL-PLA) and poly-L-lactic acid (L-PLA) or lactide. Other biodegradable, bioabsorbable polymers such as polyorthoesters, polyiminocarbonates, aliphatic polycarbonates, and polyphosphazenes may also be suitable, and other non-degradable polymers capable of carrying and delivering therapeutic drugs may also be suitable. Examples of non-degradable synthetic polymers are Parylene®, Parylast® (from Advanced Surface Technology of Billerica, Mass.), polyurethane, polyethylene, polyethylene teraphthalate, ethylene vinyl acetate, silicone and polyethylene oxide (PEO). Additional polymer material forming the polymeric sleeve portion includes polymers such as ePTFE, polyurethanes, polyether-urethanes, polyesterurethanes, ultra high molecular weight polyethylene, polypropylene, thermoplastic elastomer (C-flex), polyether-amide thermoplastic elastomer (Pebax), fluoroelastomers, fluorosilicone elastomer, styrene-isoprene-styrene rubber, styrene-butadiene-styrene rubber, polyisoprene, neoprene (polychloroprene), ethylene-propylene elastomer, chlorosulfonated polyethylene elastomer, butyl rubber, polybutadiene, polysulfide elastomer, polyacrylate elastomer, nitrile, rubber, a family of elastomers composed of styrene, ethylene, propylene, aliphatic polycarbonate polyurethane, polymers augmented with antioxidants, polymers augmented with image enhancing materials, polymers having a proton (H+) core, polymers augmented with protons (H+), butadiene and isoprene (Kraton) and polyester thermoplastic elastomer (Hytrel).

The polymer or a combination of polymers that are applied thereto are selected for their ability to optionally carry and release, at a controlled rate, various therapeutic agents such as antithrombogenic or antiproliferative drugs to further control local thrombosis. If the use of therapeutic drugs or agents is desired, the therapeutic drugs or agents are loaded at desired concentration levels per methods well known in the art to render the device ready for implantation. Examples of therapeutic drugs or agents that can be combined with the polymeric materials include antiplatelets, anticoagulants, antifibrins, antithrombins, and anti-proliferatives. Examples of antiplatelets, anticoagulants, antifibrins, and anti-thrombins include, but are not limited to, sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antibody, recombinant hirudin, thrombin inhibitor (available from Biogen located in Cambridge, Mass.), and 7E-3B® (an antiplatelet drug from Centocor located in Malvern, Pa.). Examples of cytostatic or antiproliferative agents include angiopeptin (a somatostatin analogue from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as to PDGF receptors), nitroprusside, phosphodiesterase inhibitors, prostaglandin inhibitor (available from GlaxaSmithKline, Glaxo Wellcome, UK Ltd. located in the United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon and genetically engineered epithelial cells, for example.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents are known in the art. Furthermore, the calculation of dosages, dosage rates and appropriate duration of treatment are previously known in the art.

FIG. 8 illustrates the effect on fibrous cap stress of the integration of the polymeric sleeve and the associated neointimal growth into the existing fibrous cap of the vulnerable plaque. This stress is predicted by using finite element analysis to simulate a fibroatheroma with a 60% stenosis by diameter (40% of the cross-sectional plaque area consists of lipid with a fibrous cap thickness of 65 microns) treated with a device containing a 60 micron ePTFE polymeric sleeve thickness. The predicted stress for this configuration is coMPared to the experimentally determined ultimate stress for plaque fibrous cap tissue acquired by Lendon et al. (1993), which is incorporated in its entirety by reference herein. This study indicated that ultimate stress of nonulcerated plaque caps under uniaxial loading is in the range of 0.2-0.3 MPa. FIG. 8 depicts that the integration of the polymeric sleeve and the associated neointimal growth into the existing fibrous cap decreases the maximum principal stress in the cap at average systolic blood pressure (120 mm Hg) to a level below this ultimate stress measured by Lendon et al.

The aforedescribed illustrative embodiments, including the first and second metallic portions 36, 38, interconnected by the polymeric sleeve portion 26 of the stent assembly 10, and similar stent structures can be made in many ways. One method of making the stent rings 11 is to cut a thin-walled tubular member, such as stainless steel tubing to remove portions of the tubing in the desired pattern for the stent, leaving relatively untouched the portions of the metallic tubing which are to form the rings. In accordance with the invention, it is preferred to cut the tubing in the desired pattern using a machine-controlled laser.

The tubing may be made of suitable biocoMPatible material such as stainless steel, cobalt-chromium (CoCr, NP35N), titanium, nickel-titanium (NiTi), and similar alloys. The stainless steel tube may be Alloy type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00-19.00% |
| Nickel (Ni) | 13.00-15.50% |
| Molybdenum (Mo) | 2.00-3.00% |
| Nitrogen (N) | 0.10% max. |
| Copper (Cu) | 0.50% max. |
| Iron (Fe) | Balance |

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch.

The tubing is put in a rotatable collet fixture of a machine-controlled apparatus for positioning the tubing relative to a laser. According to machine-encoded instructions, the tubing is rotated and moved longitudinally relative to the laser which is also machine-controlled. The laser selectively removes the material from the tubing by ablation and a pattern is cut into the tube. The tube is therefore cut into the discrete pattern of the finished cylindrical rings.

Cutting a fine structure (about 0.0035 inch web width) heat input and the ability to manipulate the tube with precision. It is also necessary to support the tube yet not allow the stent structure to distort during the cutting operation. In one embodiment, the tubes are made of stainless steel with an outside diameter of 0.060 inch to 0.095 inch and a wall thickness of 0.002 inch to 0.004 inch. These tubes are fixtured under a laser and positioned utilizing a CNC to generate a very intricate and precise pattern. Due to the thin wall and the small geometry of the stent pattern (0.0035 inch typical strut or ring width), it is necessary to have very precise control of the laser, its power level, the focused spot size, and the precise positioning of the laser cutting path.

In order to minimize the heat input into the stent structure, which prevents thermal distortion, uncontrolled burn out of the metal, and metallurgical damage due to excessive heat, and thereby produces a smooth debris free cut, a Q-switched Nd/YAG, typically available from Quantronix of Hauppauge, N.Y., that is frequency doubled to produce a green beam at 532 nanometers is utilized. Q-switching produces very short pulses (<100 nS) of high peak powers (kilowatts), low energy per pulse ($\leq$3 mJ), at high pulse rates (up to 40 kHz). The frequency doubling of the beam from 1.06 microns to 0.532 microns allows the beam to be focused to a spot size that is 2 times smaller, therefore increasing the power density by a factor of 4 times. With all of these parameters, it is possible to make smooth, narrow cuts in the stainless tubes in very fine geometries without damaging the narrow struts that make up to stent structure. Hence, the system makes it possible to adjust the laser parameters to cut narrow kerf width which will minimize the heat input into the material.

The positioning of the tubular structure requires the use of precision CNC equipment such as that manufactured and sold by Anorad Corporation. In addition, a unique rotary mechanism has been provided that allows the computer program to be written as if the pattern were being cut from a flat sheet. This allows both circular and linear interpolation to be utilized in programming. Since the finished structure of the stent is very small, a precision drive mechanism is required that supports and drives both ends of the tubular structure as it is cut. Since both ends are driven, they must be aligned and precisely synchronized, otherwise the stent structure would twist and distort as it is being cut.

The optical system which expands the original laser beam, delivers the beam through a viewing head and focuses the beam onto the surface of the tube, incorporates a coaxial gas jet and nozzle that helps to remove debris from the kerf and cools the region where the beam interacts with the material as the beam cuts and vaporizes the metal. It is also necessary to block the beam as it cuts through the top surface of the tube and prevent the beam, along with the molten metal and debris from the cut, from impinging on the opposite surface of the tube.

In addition to the laser and the CNC positioning equipment, the optical delivery system includes a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream that surrounds the focused beam and is directed along the beam axis. The coaxial gas jet nozzle (0.018 inch I.D.) is centered around the focused beam with approximately 0.010 inch between the tip of the nozzle and the tubing. The jet is pressurized with oxygen at 20 psi and is directed at the tube with the focused laser beam exiting the tip of the nozzle (0.018 inch dia.) The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision. In order to prevent burning by the beam and/or molten slag on the far wall of the tube I.D., a stainless steel mandrel (approx. 0.034 inch dia.) is placed inside the tube and is allowed to roll on the bottom of the tube as the pattern is cut. This acts as a beam/debris block protecting the far wall I.D.

Alternatively, this may be accomplished by inserting a second tube inside the stent tube which has an opening to trap the excess energy in the beam (which is transmitted through the kerf) along with collecting the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied creating a small jet that would force the debris out of the laser cut kerf from the inside out. This would eliminate any debris from forming or collecting on the inside of the stent structure. It would place all the debris on the outside. With the use of special protective coatings, the resultant debris can be easily removed.

In most cases, the gas utilized in the jets may be reactive or non-reactive (inert). In the case of reactive gas, oxygen or compressed air is used. Compressed air is used in this application since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approx. 0.0005 inch) with the molten slag re-solidifying along the cut. This traps the cut out scrap of the pattern requiring further processing. In order to remove the slag debris from the cut allowing the scrap to be removed from the remaining stent pattern, it is necessary to soak the cut tube in a solution of HCl for approximately 8 minutes at a temperature of approximately 55° C. Before it is soaked, the tube is placed in a bath of alcohol/water solution and ultrasonically cleaned for approximately 1 minute to remove the loose debris left from the cutting operation. After soaking, the tube is then ultrasonically cleaned in the heated HCl for 1-4 minutes depending upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. At completion of this process, the stent structures are rinsed in water. They are now ready for electropolishing.

The stent rings are preferably electrochemically polished in an acidic aqueous solution such as a solution of ELECTRO-GLO #300, sold by the ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110-135° F. and the current density is about 0.4 to about 1.5 amps per in.$^2$. Cathode to anode area should be at least about two to one.

Direct laser cutting produces edges which are essentially perpendicular to the axis of the laser cutting beam, in contrast with chemical etching and the like which produce pattern edges which are angled. Hence, the laser cutting process essentially provides strut cross-sections, from cut-to-cut, which are square or rectangular, rather than trapezoidal.

The foregoing laser cutting process to form the cylindrical rings 11 can be used with other metals including cobalt-chromium, titanium, tantalum, nickel-titanium, and other biocoMPatible metals suitable for use in humans, and typically used for intravascular stents. Further, while the formation of the cylindrical rings is described in detail, other processes of forming the rings are possible and are known in the art, such as by using chemical etching, electronic discharge machining, stamping, and other processes.

While the invention has been described in connection with certain disclosed embodiments, it is not intended to limit the scope of the invention to the particular forms set forth, but, on the contrary it is intended to cover all such alternatives, modifications, and equivalents as may be included in the spirit and scope of the invention as defined by the appended claims.

What is claimed is:

1. An intravascular stent assembly for treating vulnerable plaque within a body lumen, comprising:
   a polymeric sleeve portion in a tubular configuration having first and second ends, wherein the first end is attached to a first stent and the second end is attached to a second stent and wherein a substantial portion of said polymeric sleeve portion is unsupported by a stent structure, wherein the stent assembly includes at least two polymeric sleeve portions, wherein the at least two polymeric sleeve portions are interconnected by three stents to form the stent assembly; and
   wherein the polymeric sleeve is loaded with at least one therapeutic drug or agent and is configured to appose a vulnerable plaque region when the stent is deployed within a body lumen having a region of vulnerable plaque.

2. An intravascular stent assembly for treating vulnerable plaque within a body lumen, comprising:

a polymeric sleeve portion in a tubular configuration having first and second ends, wherein the first end is attached to a first stent and the second end is attached to a second stent and wherein a substantial portion of said polymeric sleeve portion is unsupported by a stent structure, wherein the stent assembly includes at least three stents; and wherein the polymeric sleeve is loaded with at least one therapeutic drug or agent and is configured to appose a vulnerable plaque region when the stent is deployed within a body lumen having a region of vulnerable plaque.

* * * * *

UNITED STATES PATENT AND TRADEMARK OFFICE
CERTIFICATE OF CORRECTION

PATENT NO. : 7,572,286 B1
APPLICATION NO. : 10/144553
DATED : August 11, 2009
INVENTOR(S) : Chen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1647 days.

Signed and Sealed this

Seventh Day of September, 2010

David J. Kappos
*Director of the United States Patent and Trademark Office*